United States Patent [19] [11] 4,086,137
Nakayama et al. [45] Apr. 25, 1978

[54] PROCESS FOR THE PRODUCTION OF L-ARGININE BY FERMENTATION

[75] Inventors: Kiyoshi Nakayama, Sagamihara; Kazumi Araki, Machida; Hajime Yoshida, Sagamihara, all of Japan

[73] Assignee: Kyowa Hakko Kogyo Co., Ltd., Tokyo, Japan

[21] Appl. No.: 766,630

[22] Filed: Feb. 8, 1977

[30] Foreign Application Priority Data

Feb. 18, 1976  Japan .................................. 51-15737

[51] Int. Cl.$^2$ ............................................. C12D 13/06
[52] U.S. Cl. ........................................ 195/29; 195/47
[58] Field of Search ...................................... 195/47, 29

[56] References Cited

U.S. PATENT DOCUMENTS 3,734,829  5/1973  Chibata et al. .......................... 195/47

*Primary Examiner*—Alvin E. Tanenholtz
*Attorney, Agent, or Firm*—Fitzpatrick, Cella, Harper & Scinto

[57] ABSTRACT

L-arginine is produced by fermentation of a microorganism belonging to the genus Bacillus capable of producing L-arginine and having a nutritional requirement for at least one compound of the group consisting of methionine, histidine, threonine, proline, isoleucine, lysine, adenine, guanine and uracil or its precursor. L-arginine is accumulated in the culture liquor and may be recovered therefrom.

9 Claims, No Drawings

PROCESS FOR THE PRODUCTION OF L-ARGININE BY FERMENTATION

BACKGROUND OF THE INVENTION

L-arginine is an amino acid classified as essential with respect to its growth effect in rats. The amino acid is also useful inter alia as a starting compound in the preparation of arginine glutamate which is an adjunct in management of ammonium intoxication due to hepatic failure.

Heretofore, L-arginine has been prepared using various methods. For example the L-form has been obtained by hydrolysis of proteins. In industrial practice it is precipitated from gelatine hydrolyzate as the flavianate.

As for processes for the production of L-arginine by fermentation using a microorganism of the genus Bacillus, processes using strains which are resistant to arginine analogues are known as described in Applied Microbiology Vol. 32, P. 987 (1971) and Japanese Patent Publication No. 25359/74. Further, as for the production of L-arginine by a microorganism having a nutritional requirement, Japanese Unexamined Patent Application published under No. 61388/74 discloses the production of L-arginine by a strain of the genus Brevibacterium having a requirement for guanine.

However, natural processes which have a high yield of L-arginine are in demand for utilization in industrial practice. To this end, it has been found that improved yields of L-arginine may be attained by fermenting certain auxotrophic mutants of the genus Bacillus.

SUMMARY OF THE INVENTION

In accordance with the present invention, increased yields of L-arginine are produced by culturing a strain of microorganism belonging to the genus Bacillus capable of producing L-arginine and having a nutritional requirement (including the so-called "leaky" type) for at least one member of the group consisting of methionine, histidine, threonine, proline, isoleucine, lysine, adenine, quanine and uracil (or its precursor) in a nutrient medium; accumulating L-arginine in the culture liquor and recovering the L-arginine therefrom.

"Nutrition-requirement" is a term well-known in the art. A nutrition-requiring mutant cannot grow as well as the parent strain in a minimum medium in which the parent strain propagates well, but can grow as well as the parent in a minimum medium to which a specific nutrient is added. Such mutants are characterized as auxotrophic.

As stated above, the present invention also contemplates the so-called "leaky" type of mutant wherein the nutritional requirement is not absolute.

DESCRIPTION OF THE INVENTION

In accordance with the present invention, L-arginine is produced and accumulated in a culture liquor obtained by fermenting an L-arginine-producing strain described below in an ordinary nutrient medium. The elaborated L-arginine is readily isolated and recovered from the culture liquor.

As the L-arginine-producing strain used in the present invention, any mutant may be used so long as it is obtained by endowing a nutritional requirement (including the so-called "leaky" type) for at least one of methionine, histidine, threonine, proline, isoleucine, lysine, adenine, guanine, uracil or a precursor of uracil, to a strain of microorganism belonging to the genus Bacillus which has the ability to produce L-arginine.

Candidate strains for mutation are selected from strains of the genus Bacillus which are capable of producing L-arginine. Particularly, an L-arginine-producing strain of the genus Bacillus which is resistant to arginine analogues such as canavanine, homoarginine, D-arginine and arginine hydroxamate or histidine analogues such as 2-thiazolealanine is preferred.

Of strains of the genus Bacillus, those which belong to the species Bacillus subtilis have been found to be preferred.

The strains listed below are examples of mutants suitable for the present invention, which are obtained by mutating the arginine-producing parent strain, Bacillus subtilis 110M-59 (prototrophic arginine hydroxamate-resistant strain) (ATCC 31193) derived from Bacillus subtilis ATCC 15244 (wild strain) by conventional methods for inducing mutation. The following specific exemplary strains have been deposited with the American Type Culture Collection, Rockville, Md., U.S.A. and have been accorded the noted accession numbers. These strains are freely available to the public.

| Strain | ATCC |
|---|---|
| Bacillus subtilis BA-22 (requiring methionine) | 31185 |
| Bacillus subtilis BA-26 (requiring histidine) | 31186 |
| Bacillus subtilis BA-10 (requiring threonine) | 31184 |
| Bacillus subtilis BA-9 (requiring proline) | 31183 |
| Bacillus subtilis BA-32 (requiring isoleucine or lysine) | 31187 |
| Bacillus subtilis BA-43 (requiring adenine or guanine) | 31188 |
| Bacillus subtilis 59PL-1 (requiring uracil or orotic acid) | 31189 |

Strains suitable for the present invention may have requirements other than those mentioned above. For example, a strain endowed with a requirement for tryptophane in addition to the above-mentioned requirements may be used.

In the present invention, a mutant having the necessary requirement may be obtained by the conventional mutation inducing methods and screening techniques. For example, the above-mentioned specific mutants are obtained in the following manner. Microbial cells of the parent strain are grown on a bouillon slant medium comprising 0.5 g/dl yeast extract, 1 g/dl meat extract, 1 g/dl peptone, 0.5 g/dl NaCl and 2 g/dl agar (pH 7.2) at 30° C for 24 hours. The cells are then suspended, at a concentration of about $10^{10}$ cells per ml, in 0.05M tris-maleate buffer solution (pH 6.0) containing 2 mg/ml of N-methyl-N'-nitro-N-nitrosoguanidine, and the suspension is allowed to stand at room temperature for 20 minutes and then is subjected to centrifugation at .3000 r.p.m. for 15 minutes. Thereafter, the cells are again suspended in 0.05M tris-maleate buffer solution (pH 6.0) at the same concentration as described above. Then, 1 ml of the suspension is inoculated in 10 ml of a nutrient medium comprising 2 g/dl glucose, 1 g/dl peptone, 1 g/dl yeast extract and 0.5 g/dl NaCl (pH 7.2), and incubated at 30° C overnight and the cells are collected. The collected cells are washed with 0.05M tris-maleate buffer solution (pH 6.0) and are suspended in the same buffer solution at a concentration of about $10^{2~3}$ cells per ml. Then 0.1 ml of the suspension is smeared on an agar plate of a complete medium comprising 1 g/dl glucose, 0.5 g/dl yeast extract, 1 g/dl peptone, 0.25 g/dl NaCl and 2 g/dl agar (pH 7.2) and the cells are incubated at 30° C for 24 hours to form colonies. Cells of the resulting colonies are smeared on an agar plate of a complete medium having the same composition as the above-mentioned medium and also on an agar plate of a minimum comprising 1 g/dl glucose, 0.1 g/dl ammonium monophosphate, 0.02 g/dl potassium chloride, 0.02 g/dl magnesium sulfate, 30 γ/l biotin, 1 ml/l trace elements, 10 mg/l vitamin $B_1$ and 2 g/dl agar (pH 7.2) and are allowed to stand at 30° C for 1~2 days. The trace elements used in the latter medium are supplied by a solution comprising 88 mg sodium borate decahydrate, 37 mg ammonium molybdate tetrahydrate, 8.8 mg zinc sulfate heptahydrate, 270 mg copper sulfate pentahydrate, 7.2 mg manganese chloride tetrahydrate and 970 mg ferric chloride hexahydrate dissolved in distilled water to make 1 L.

Candidate auxotrophic strains are selected from those strains which do not grow on the agar plate of the minimum medium but do grow on the complete medium. The nutritional requirement of a selected auxotrophic mutant is determined by auxanography. Those auxotrophs which have the desired nutritional requirements are then checked for ability to produce increased yields of L-arginine; and strains having the ability are suitable for the present invention.

Media usually used in the production of amino acids by fermentation are suitable for the present invention. That is, either a synthetic medium or a natural medium may be used so long as it contains a carbon source, a nitrogen source, inorganic materials and other nutrients as shown in the examples. As the carbon source, carbohydrates such as glucose, sucrose, fructose, mannose, starch, starch hydrolyzate, blackstrap molasses, etc., glycerol, polyalcohol, organic acids such as pyruvic acid, fumaric acid, lactic acid, acetic acid, etc., alcohols such as ethanol, methanol, etc., amino acids such as glutamic acid, aspartic acid, etc., and n-paraffins and other hydrocarbons may be used. As the nitrogen source, ammonia, inorganic and organic ammonium salts such as ammonium chloride, ammonium sulfate, ammonium carbonate, ammonium acetate, etc., urea and other nitrogen-containing compounds, and natural substances such as peptone, meat extract, yeast extract, corn steep liquor, casein hydrolyzate, fish meal, digest of fish meal, defatted soybean cake, digest of defatted soybean cake, chrysalis hydrolyzate, etc. may be used. As inorganic materials, potassium phosphate, magnesium sulfate, sodium chloride, ferrous sulfate, manganese sulfate, calcium carbonate, etc. are appropriate.

The medium must, of course, be supplemented with an appropriate amount of the nutrients required by the particular microorganism for growth. In some cases, these nutrients are supplied as components of natural substances which are used as the nitrogen source.

In the present invention, the productivity of L-arginine by the auxotrophic strain can be further enhanced by adding L-glutamic acid to the fermentation medium either at the start of the fermentation or during the growth phase of the cells. In either case, it is preferable to add a total amount of L-glutamic acid to make up 0.1~3% (W/V) of the medium.

Culturing is carried out under aerobic conditions, for example by shaking culture, agitation submerged culture or the like. The preferred temperature for culturing is generally 20°~40° C, but culturing can be carried out at a temperature which is out of this range so long as the particular microorganism can grow. In order to obtain a high yield of the product, it is desirable that the pH of the medium be maintained at around neutral during culturing. Usually after culturing for 1 to 5 days under these conditions, a considerable amount of L-arginine is produced and accumulated in the culture liquor.

After the completion of culturing, the microbial cells and any precipitate are removed from the culture liquor by conventional methods. Then the L-arginine is recovered from the culture liquor by known methods such as an ion exchange resin treatment described in Example 1.

Practice of certain specific embodiments of the invention is illustrated by the following representative examples.

EXAMPLE 1

In this example, a nutrient medium having the following composition is poured into large test tubes in 5 ml portions and sterilized.

| | | |
|---|---|---|
| blackstrap molasses | 10 | g/dl (as glucose) |
| ammonium sulfate | 3 | g/dl |
| urea | 0.3 | g/dl |
| potassium dihydrogen phosphate | 0.05 | g/dl |
| dipotassium hydrogen phosphate | 0.05 | g/dl |
| magnesium sulfate | 0.025 | g/dl |
| corn steep liquor | 0.5 | g/dl |
| (pH 7.2) | | |

Each of the strains identified in Table 1 and their arginine-producing parent strain, i.e. Bacillus subtilis 110M-59 (Prototrophic arginine hydroxamate-resistant strain) are seed cultured in a seed medium comprising 2 g/dl glucose, 1 g/dl peptone, 1 g/dl yeast extract and 0.5 g/dl sodium chloride (pH 7.2) at 30° C for 24 hours. Each seed culture is then inoculated in a ratio of 10% into a test tube containing the nutrient medium and cultured with shaking at 30° C for 96 hours. At the completion of cultures, L-arginine is accumulated in the culture liquors in the amounts shown in Table 1.

As an example of the isolation procedure, the bacterial cells and other insoluble materials are removed from the culture liquor of Bacillus subtilis BA-22 (ATCC 31185) to obtain a filtrate. Then 1 L of the filtrate is passed through a column packed with a strongly acidic ion exchange resin [Amberlite IR-120B (Na type), Trademark, produced by Rohm & Haas Co.] to adsorb the L-arginine. After washing, the L-arginine is eluted out and is isolated and purified according to the conventional methods. As the result, 3.8 g of L-arginine in crystalline form is obtained.

Table 1

| Strain | Requirement | Amount of L-arginine (mg/ml) |
|---|---|---|
| Bacillus subtilis BA-22 | methionine | 5.8 |
| Bacillus subtilis BA-26 | histidine | 4.5 |
| Bacillus subtilis BA-10 | threonine | 4.7 |
| Bacillus subtilis BA-9 | proline | 4.1 |
| Bacillus subtilis BA-32 | isoleucine or lysine | 4.0 |
| Bacillus subtilis BA-43 | adenine or guanine | 4.0 |
| Bacillus subtilis 59PL-1 | uracil or orotic acid | 3.8 |
| Bacillus subtilis 110M-59 (parent strain) | none | 3.0 |

EXAMPLE 2

In this example, culturing is carried out in the same manner as in Example 1 except that the strains shown in Table 2 are used as the seed strains and 1.5 g/dl of monosodium glutamate is added to the fermentation medium. As a result, L-arginine is accumulated in the culture liquor in the amounts shown in Table 2.

Table 2

| Strain | Requirement | Amount of L-arginine (mg/ml) |
| --- | --- | --- |
| *Bacillus subtilis* BA-22 | methionine | 6.2 |
| *Bacillus subtilis* BA-26 | histidine | 5.7 |
| *Bacillus subtilis* 110M-59 (parent strain) | none | 3.9 |

As will be appreciated from the above, the present invention provides a method for the production of L-arginine in significantly increased yields.

What is claimed is:

1. A process for producing L-arginine which comprises culturing a mutant strain of microorganism derived from an L-arginine producing strain belonging to the genus Bacillus, said mutant having a nutritional requirement for at least one member of the group consisting of methionine, histidine, threonine, proline, isoleucine, lysine, adenine, guanine, uracil and precursors of uracil in a nutrient medium until L-arginine is formed in the culture liquor, and thereafter isolating said L-arginine therefrom.

2. A process according to claim 1 wherein said nutrient medium contains from 0.1 to 3% L-glutamic acid.

3. A process according to claim 1 wherein said culturing is carried out at a temperature of from 20° to 40° C for 1 to 5 days.

4. A process according to claim 1 wherein said mutant strain belongs to the species Bacillus subtilis.

5. A process according to claim 1 wherein said mutant strain is selected from the group consisting of *Bacillus subtilis* ATCC 31183, *Bacillus subtilis* ATCC 31184, *Bacillus subtilis* ATCC 31185, *Bacillus subtilis* ATCC 31186, *Bacillus subtilis* ATCC 31187, *Bacillus subtilis* ATCC 31188, and *Bacillus subtilis* ATCC 31189.

6. A process for the production of L-arginine which comprises mutating a parent microorganism belonging to the genus Bacillus to acquire a nutritional requirement for at least one member selected from the group consisting of methionine, histidine, threonine, proline, isoleucine, lysine, adenine, guanine, uracil, and precursors or uracil; culturing said mutant in a nutrient medium until L-arginine is formed in the culture liquor and thereafter isolating said L-arginine therefrom.

7. A process according to claim 6 wherein said parent strain is resistant to arginine anaogues.

8. A process according to claim 6 wherein said nutrient medium contains from 0.1 to 3% L-glutamic acid.

9. A process according to claim 6 wherein said culturing is carried out at a temperature of from 20° to 40° C for 1 to 5 days.

* * * * *

UNITED STATES PATENT AND TRADEMARK OFFICE
CERTIFICATE OF CORRECTION

PATENT NO. : 4,086,137
DATED : April 25, 1978
INVENTOR(S) : Kiyoshi Nakayama, et al.

It is certified that error appears in the above-identified patent and that said Letters Patent are hereby corrected as shown below:

Col. 1, line 42, "quanine" should be --guanine--;

Col. 3, line 8, after "minimum" insert --medium--;

Col. 6, line 26, "anaogues" should be --analogues--.

Signed and Sealed this

Twenty-second Day of August 1978

[SEAL]

Attest:

RUTH C. MASON
Attesting Officer

DONALD W. BANNER
Commissioner of Patents and Trademarks